United States Patent
Fujiwara et al.

(10) Patent No.: US 6,309,526 B1
(45) Date of Patent: *Oct. 30, 2001

(54) BIOSENSOR

(75) Inventors: Masaki Fujiwara, Onsen-gun; Yoshinobu Tokuno, Iyo-gun; Shoji Miyazaki, Matsuyama, all of (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/384,103

(22) Filed: Aug. 26, 1999

Related U.S. Application Data

(62) Division of application No. 08/889,929, filed on Jul. 10, 1997, now Pat. No. 6,004,441.

(51) Int. Cl.⁷ .................................................. G01N 27/26
(52) U.S. Cl. ......................... 204/403; 204/416; 427/2.13
(58) Field of Search .................................. 204/412, 403; 427/2.11, 2.13

(56) References Cited

U.S. PATENT DOCUMENTS 5,834,224 * 11/1998 Ruger et al. ........................ 435/14
6,004,441 * 12/1999 Fujiwara et al. ................... 204/412

* cited by examiner

*Primary Examiner*—T. Tung
*Assistant Examiner*—Alex Noguerola
(74) *Attorney, Agent, or Firm*—Ratner & Prestia

(57) ABSTRACT

A biosensor is fabricated by forming a metal film over the surface of a substrate through evaporation, sputtering or by gluing a metal foil, then splitting the metal film into three regions, and forming a reagent layer on an area of measuring electrode and two counter-electrodes for placing a liquid sample on by providing a cover disposed over the splitted metal film. As neither of the electrodes are formed through conventional printing technology, the electrodes can be formed without dispersion. As a result, a precision biosensor having excellent response characteristics is implemented.

2 Claims, 2 Drawing Sheets

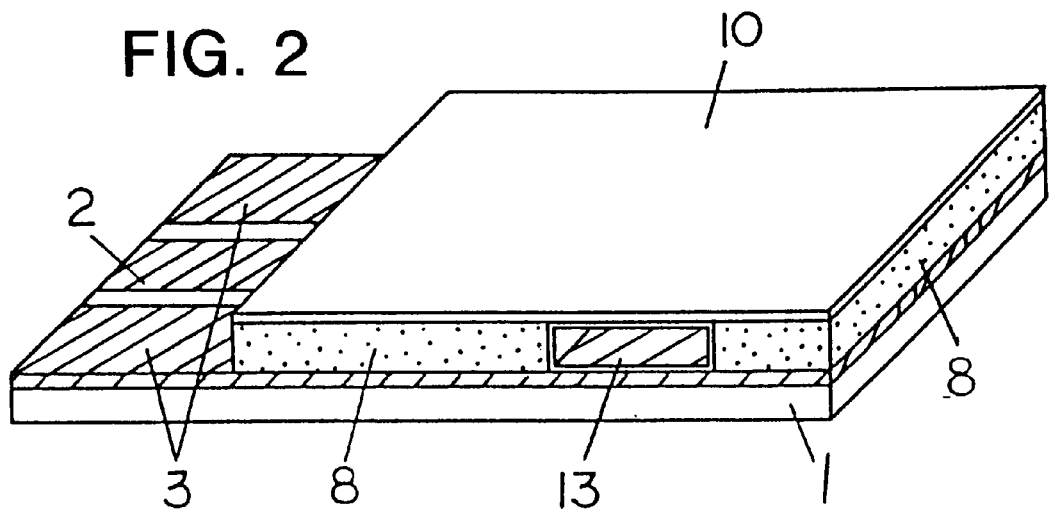
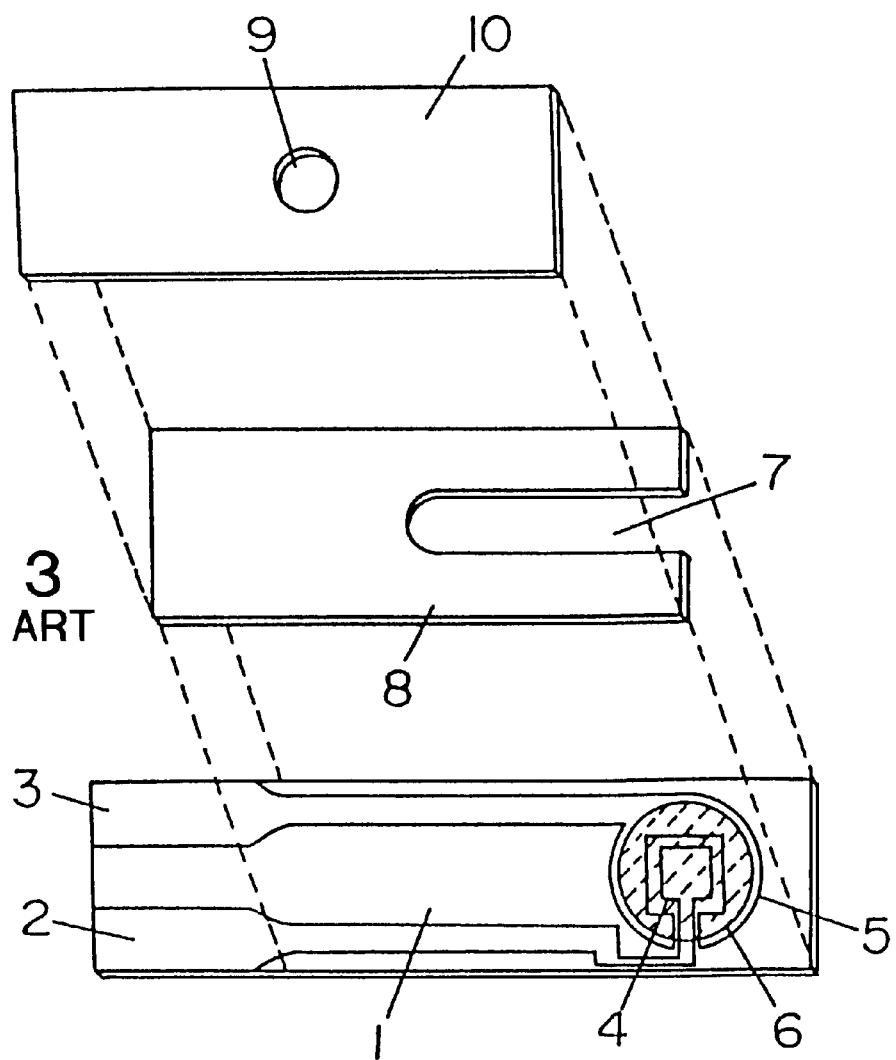

BIOSENSOR

This application is a Divisional Application of U.S. patent application Ser. No. 08/889,929 filed Jul. 10, 1997, now U.S. Pat. No. 6,004,441.

FIELD OF THE INVENTION

The present invention relates to a biosensor for quantifying a specific component contained in a liquid sample. Specifically a method is disclosed for simplifying manufacturing of a biosensor and improving the accuracy of measurement.

BACKGROUND OF THE INVENTION

Among the conventional biosensors is a biosensor for measuring the density of glucose in blood, as disclosed in the Japanese Patent Publication No. 5-256811. The conventional sensor comprises, as shown in FIG. 3, leads 2 and 3 formed on an insulating substrate 1 by a screen-printing technology, and a measuring electrode 4 and a counter-electrode 5, coupled respectively with leads. On the measuring electrode 4 and the counter-electrode 5 is a reagent layer 6 comprised of glucose oxidase as an enzyme, potassium ferricyanide as a mediator, etc.

On the insulating substrate 1, a cover 10 having an air hole 9 is attached with a spacer 8 having a void 7 at one end in between. These components constitute a biosensor.

For measuring the blood glucose density using a conventional biosensor having the above described constitution, one end of a capillary formed by the void 7 of spacer 8 is placed on blood, then the blood is sucked into the capillary by a capillary phenomenon with the other end of the capillary forming an air hole 9, and the reagent layer 6 is resolved causing an oxidation/reduction. If a voltage is applied between measuring electrode 4 and counter-electrode 5, electric current flows in proportion to the density of glucose. The blood sugar level is thus measured.

In the conventional biosensor, carbon is employed as an electrode material suitable for the potassium ferricyanide mediator. The electrode is formed through screen-printing technology.

Namely, a silver paste is screen-printed on substrate 1 for forming the leads 2 and 3, and a carbon paste is screen-printed to form the measuring electrode 4 and the counter-electrode 5. Then, in order to regulate the effective area of measuring electrode 4, a resist layer is formed on the electrode and the leads by screen-printing an insulating paste.

In a conventional manufacturing method wherein a screen-printing process is employed a plurality of times, drying time is needed after each of the steps of paste preparation and screen-printing. The drying thus increases manufacturing time.

Furthermore, in printing the insulating paste, it is inevitable that some paste will ooze out as a result. A wide dispersion in the area of measuring electrode 4 and an adverse influence on the accuracy of response of the finished biosensor will result. Therefore, a need exists to develop a simpler method of providing an measuring electrode, while at the same time enabling a biosensor of higher measuring accuracy to be obtained.

SUMMARY OF THE INVENTION

A biosensor according to the present invention comprises an insulating substrate having a surface which is covered with a metal film. The metal film is split into a plurality of strips. Two covers are placed above the strips. The covers are separated. The portions of the strips between the two covers serve as a measuring electrode and two counter electrodes. The strips at one end of the electrode serve as leads for supplying voltage. A reagent layer is formed between the two covers.

By manufacturing a biosensor as described above, the areas of the measuring electrode and counter-electrode are not dispersed. Therefore, dispersion in response characteristics is reduced.

Furthermore, the upper surface of one of the covers is sealed with a top cover to form a capillary with the openings at both sides of the body of a biosensor. With the above described constitution, as a certain fixed amount of a liquid sample is introduced into the capillary, high accuracy is assured, and as the opening of the capillary is provided at both sides of a biosensor, a liquid sample may be supplied from either side for increased convenience.

Thus, according to the present invention, the area of electrode is defined precisely. In this manner, high accuracy of measurement is obtained. Further, because either opening can be used to supply the liquid sample, high convenience is obtained.

BRIEF DESCRIPTION OF THE DRAWINGS

FIG. 2 is a perspective view of a biosensor according to a further exemplary embodiment of the present invention.

FIG. 3 is an exploded view of a biosensor in accordance with the prior art.

DESCRIPTION OF THE PREFERRED EMBODIMENTS

A biosensor according to an exemplary embodiment of the present invention is described in the following with reference to the drawings. Those components having the same respective functions as found in a conventional biosensor are identified with the same numbers.

Figure 1A:
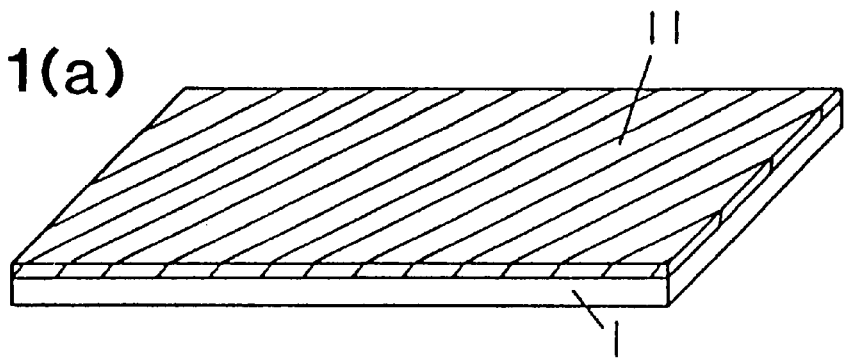
FIGS. 1(a)–(d) are perspective views of a biosensor according to an examplary embodiment of the present invention, shown in the sequence of its manufacturing steps.

As shown in FIG. 1(a), a metal film 11 is formed over a surface of an insulating substrate 1 made of, for example, polyethylene terephthalate. Dimensions of the substrate 1 may approximately be, for example, 35 mm long×6 mm wide×0.7 mm high, and the thickness of the metal film 11 may be 5–10 nm.

Metal film 11 may be formed either by evaporation, sputtering or by gluing a metal foil over substrate 1. As a material for the metal film 11, Pt group materials such as Pd, Pt, Ru are appropriate when potassium ferricyanide is used as a mediator; other materials may be chosen depending upon the mediator used.

Figure 1B:
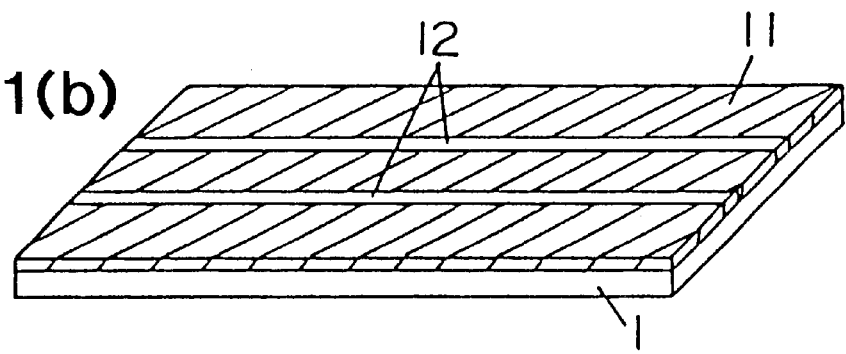

Next, as shown in FIG. 1(b) the metal film 11 is split into three regions by providing two parallel slits 12 in the metal film 11 on substrate 1 by a laser, such as a YAG laser or by other methods of producing smooth or linear edges (e.g. micro machining technology). The width of the slits 12 may be, for example, 70 µm. In this manner, each region (or portion thereof) may have substantially smooth or linear (e.g. straight) edges.

Figure 1C:
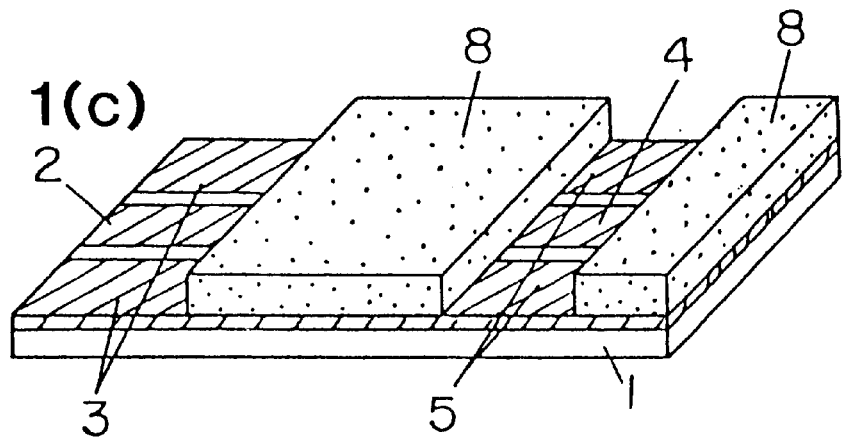
Figure 1D:
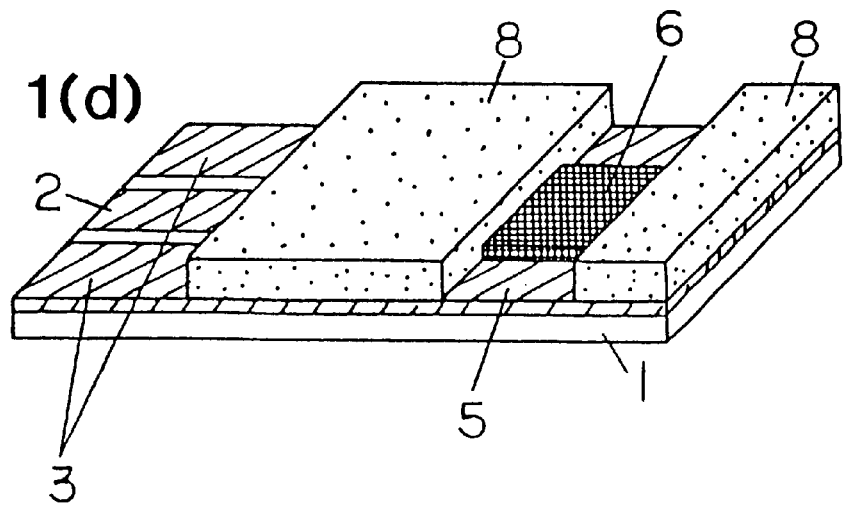

Next, as shown in FIG. 1(c), two covers 8 comprised of an insulating film such as polyethylene terephthalate, are provided across the 3-strip metal film 11 to form a space between the two covers 8. The sample (e.g. blood) is to be placed in the space. The metal film in the middle of the space serve as a measuring electrode 4, and the metal films at both sides of the space serve as counter-electrodes 5. Again, the metal films (for example, in the space) may be formed with substantially smooth or linear (e.g. straight) edges. The metal films exposed on the other end of substrate 1 serve as leads 2 and 3 for supplying voltage to measuring electrode 4 and counter-electrode 5, respectively, which are to be connected to an external power supply (not shown).

In order to improve the performance of a biosensor, the width of each of the two counter-electrodes 5 should preferably be identical or larger than that of the measuring electrode 4.

As shown in FIG. 1(*d*), a reagent layer 6 is provided over the measuring electrode 4 and the two counter-electrodes 5. In the case of biosensor for measuring blood sugar level (for example), a reagent comprised of (for example) glucose oxidase as an enzyme, and potassium ferricyanide as a mediator, is used as the reagent layer 6.

A method of measurement using the biosensor described above explained with regard to glucose density measurements. A drop of blood is placed on reagent layer 6 with the two couter-electrodes 5 already energized. The electro-conductivity between the counter-electrodes changes accordingly.

After the blood is placed, application of voltage is suspended for a certain specific time while waiting for the oxidation of glucose contained in blood and the accompanying reduction of potassium ferricyanide to take place. A voltage is applied on measuring electrode 4 and counter-electrode 5 through respective leads 2 and 3 after a certain specific time passed. Then, the reduced potassium ferricyanide is oxidized and flow of an electric current is generated in proportion to the density of glucose. The blood sugar level is thus measured.

As described above, a biosensor according to the exemplary embodiment of the present invention is fabricated through a simplified manufacturing procedure; leads 2, 3 and measuring electrode 4 and counter-electrode 5 are shaped by forming a metal film 11 on substrate 1, providing slits 12 in the metal film, and gluing a cover 8. As compared with the conventional procedure in which a screen-printing process is repeatedly employed, the present method is much simpler. Furthermore, as the measuring electrode 4 is formed surrounded by the laser-cut slits 12 (or other method of cutting) and the edge of cover 8, the area of measuring electrode 4 is defined with much higher precision than that provided by screen-printing technology. This makes it possible to present biosensors whose dispersion in measurement accuracy is significantly suppressed.

FIG. 2 shows a biosensor according to another exemplary embodiment of the present invention; a capillary 13 is formed by providing an insulating top cover 10 of polyethylene terephthalate etc. over the cover 8 of the biosensor of FIG. 1. With this constitution, a biosensor receives a certain specified amount of blood by simply touching one opening of the capillary 13 with blood; the other opening works as an air hole for the capillary phenomenon. The measuring function is thus further improved. Furthermore, according to the present embodiment, a liquid sample may be received through either opening of the biosensor body.

The invention may be embodied in other specific forms without departing from the spirit or essential characteristics thereof. The scope of the invention being indicated by the the appended claims rather than by the foregoing description and all changes which come within the meaning and range of equivalency of the claims are therefore intended to be embraced therein.

We claim:

1. A biosensor comprising:

an insulating substrate having a plurality of metal strips spaced apart and formed thereon, said metal strips having a thickness of 5 to 10 nm;

a plurality of covers spaced apart and formed on said strips to form a space between two of said covers so that one of said strips in said space defines a measuring electrode and another of said strips in said space defines a counter-electrode, and a reagent layer provided over said measuring electrode and said counter-electrode.

2. A method of manufacturing a biosensor comprising the steps of:

(a) covering an insulating substrate with a plurality of metal strips so that said strips are physically separated from each other, said metal strips having a thickness of 5 to 10 nm;

(b) placing two covers separated from each other over said strips to define a measuring electrode and a counter electrode from said strips, and (c) providing a reagent layer on said measuring electrode and counter-electrode.

\* \* \* \* \*

UNITED STATES PATENT AND TRADEMARK OFFICE
CERTIFICATE OF CORRECTION

PATENT NO.     : 6,309,526 B1
DATED          : October 30, 2001
INVENTOR(S)    : Masaki Fujiwara et al.

It is certified that error appears in the above-identified patent and that said Letters Patent is hereby corrected as shown below:

<u>Title page,</u>
Item [56], insert the following references:
-- 5,437,999      8/01/95     Diebold et al.   435/287.9
   5,120,420      6/08/92     Nankai et al.    204/403
   5,336,388      8/09/94     Leader et al.    204/406 --

Signed and Sealed this

Thirteenth Day of August, 2002

*Attest:*

JAMES E. ROGAN
*Attesting Officer*        *Director of the United States Patent and Trademark Office*